United States Patent
Stone

(10) Patent No.: US 10,245,017 B2
(45) Date of Patent: *Apr. 2, 2019

(54) KNOTLESS TWIST SUTURE ANCHOR

(71) Applicant: Biomet Manufacturing, LLC, Warsaw, IN (US)

(72) Inventor: Kevin T. Stone, Winona Lake, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 214 days.

This patent is subject to a terminal disclaimer.

(21) Appl. No.: 14/292,171

(22) Filed: May 30, 2014

(65) Prior Publication Data

US 2015/0342594 A1 Dec. 3, 2015

(51) Int. Cl.
*A61B 17/00* (2006.01)
*A61B 17/04* (2006.01)

(52) U.S. Cl.
CPC .............. *A61B 17/0401* (2013.01); *A61B 2017/00004* (2013.01); *A61B 2017/00407* (2013.01); *A61B 2017/044* (2013.01); *A61B 2017/0414* (2013.01); *A61B 2017/0448* (2013.01); *A61B 2017/0496* (2013.01)

(58) Field of Classification Search
CPC ........ A61B 17/0401; A61B 2017/0414; A61B 2017/0446–2017/045; A61B 2017/0448; A61B 2017/0453; A61B 2017/0496; A61F 2002/0817; A61F 2002/0823; A61F 2002/0829; A61F 2002/0835
USPC ....................................... 606/232; 623/13.14
See application file for complete search history.

(56) References Cited

U.S. PATENT DOCUMENTS

| | | |
|---|---|---|
| 4,512,346 A | 4/1985 | Lemole |
| 4,750,492 A | 6/1988 | Jacobs |
| 4,870,957 A | 10/1989 | Goble et al. |
| 5,152,790 A | 10/1992 | Rosenberg et al. |
| 5,263,803 A | 11/1993 | Anquetin |
| 5,370,662 A | 12/1994 | Stone et al. |
| 5,383,905 A | 1/1995 | Golds et al. |
| 5,443,482 A | 8/1995 | Stone et al. |
| 5,458,601 A | 10/1995 | Young, Jr. et al. |
| 5,486,197 A | 1/1996 | Le et al. |
| 5,501,688 A | 3/1996 | Whiteside et al. |
| 5,584,835 A | 12/1996 | Greenfield |
| 5,630,824 A | 5/1997 | Hart |
| 5,919,208 A | 7/1999 | Valenti |
| 5,957,953 A | 9/1999 | DiPoto et al. |
| 6,066,160 A | 5/2000 | Colvin et al. |
| 6,086,608 A | 7/2000 | Ek et al. |
| 6,126,677 A | 10/2000 | Ganaja et al. |
| 6,200,329 B1 | 3/2001 | Fung et al. |
| 6,293,961 B2 | 9/2001 | Schwartz et al. |

(Continued)

*Primary Examiner* — Katrina M Stransky
*Assistant Examiner* — Lindsey Bachman
(74) *Attorney, Agent, or Firm* — Schwegman Lundberg & Woessner, P.A.

(57) ABSTRACT

A suture anchor includes a first body portion having a bone-engaging feature to fixedly engage a bony tissue and a second body portion including a flexible member loop for receipt of a suture where engaging the second body portion rotates the flexible member loop with respect to the first body portion. Rotation of the second body portion causes the flexible member loop to frictionally engage a suture passing through the flexible member loop to form a twist to frictionally secure the suture.

30 Claims, 8 Drawing Sheets

(56) References Cited

U.S. PATENT DOCUMENTS

| | | |
|---|---|---|
| 6,361,258 B1 | 3/2002 | Heesch |
| 6,520,980 B1 | 2/2003 | Foerster |
| 6,616,694 B1 | 9/2003 | Hart |
| 6,666,877 B2 | 12/2003 | Morgan et al. |
| 7,144,413 B2 | 12/2006 | Wilford et al. |
| 7,416,556 B2 | 8/2008 | Jackson |
| 7,674,276 B2 | 3/2010 | Stone et al. |
| 2002/0156476 A1 | 10/2002 | Wilford |
| 2003/0004545 A1 | 1/2003 | Burkhart et al. |
| 2003/0065361 A1* | 4/2003 | Dreyfuss ............ A61B 17/0401 606/232 |
| 2004/0098050 A1 | 5/2004 | Foerster et al. |
| 2004/0098052 A1 | 5/2004 | West et al. |
| 2004/0133239 A1 | 7/2004 | Singhatat |
| 2004/0138706 A1 | 7/2004 | Abrams et al. |
| 2005/0055052 A1 | 3/2005 | Lombardo et al. |
| 2005/0090827 A1 | 4/2005 | Gedebou |
| 2005/0131430 A1 | 6/2005 | Ravikumar |
| 2005/0149120 A1 | 7/2005 | Collier et al. |
| 2008/0015509 A1 | 1/2008 | Backman et al. |
| 2008/0086138 A1* | 4/2008 | Stone ................. A61B 17/0401 606/265 |
| 2012/0179199 A1* | 7/2012 | Hernandez ......... A61B 17/0401 606/232 |
| 2013/0090731 A1* | 4/2013 | Walker ............... A61B 17/0401 623/13.14 |

* cited by examiner

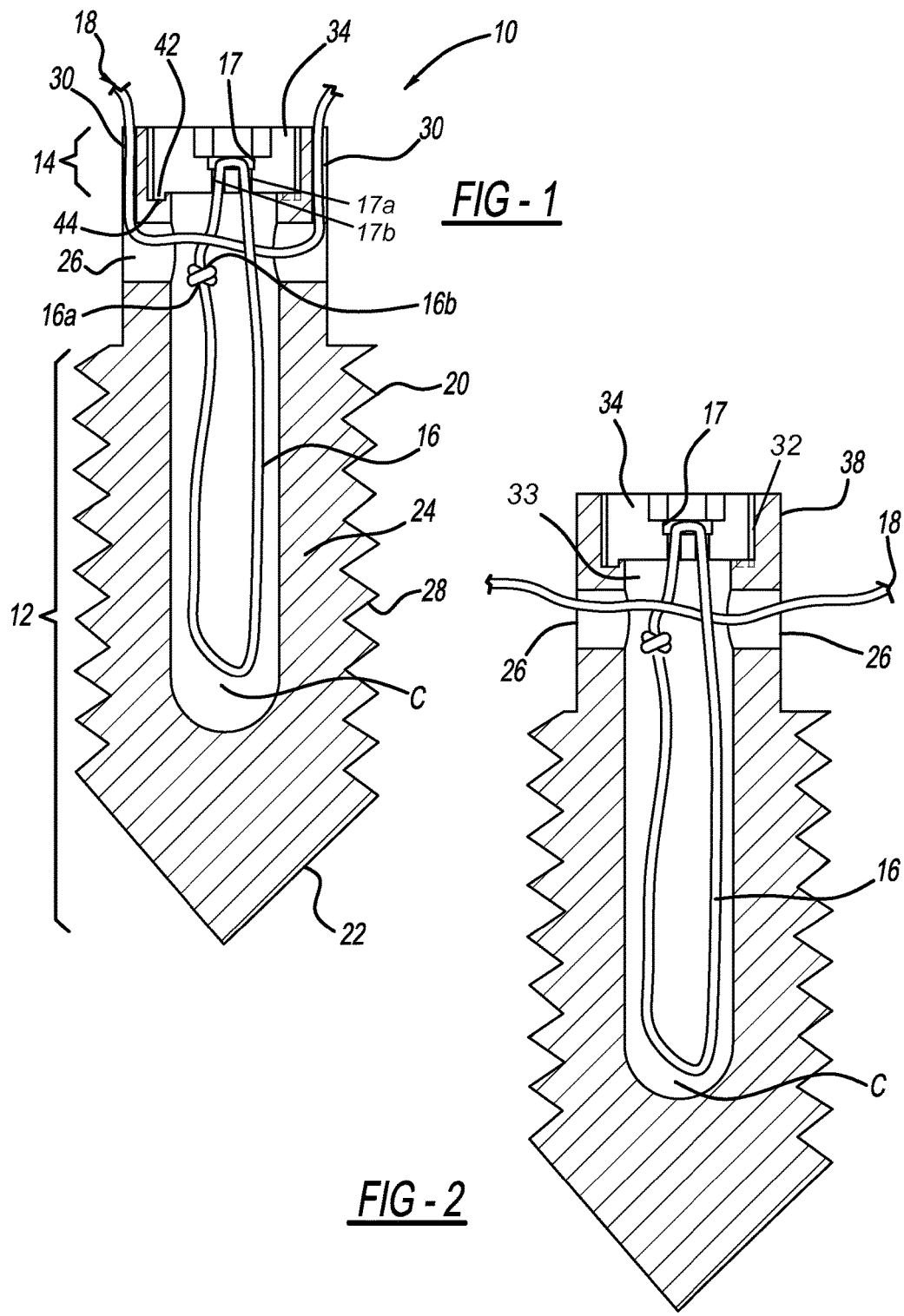

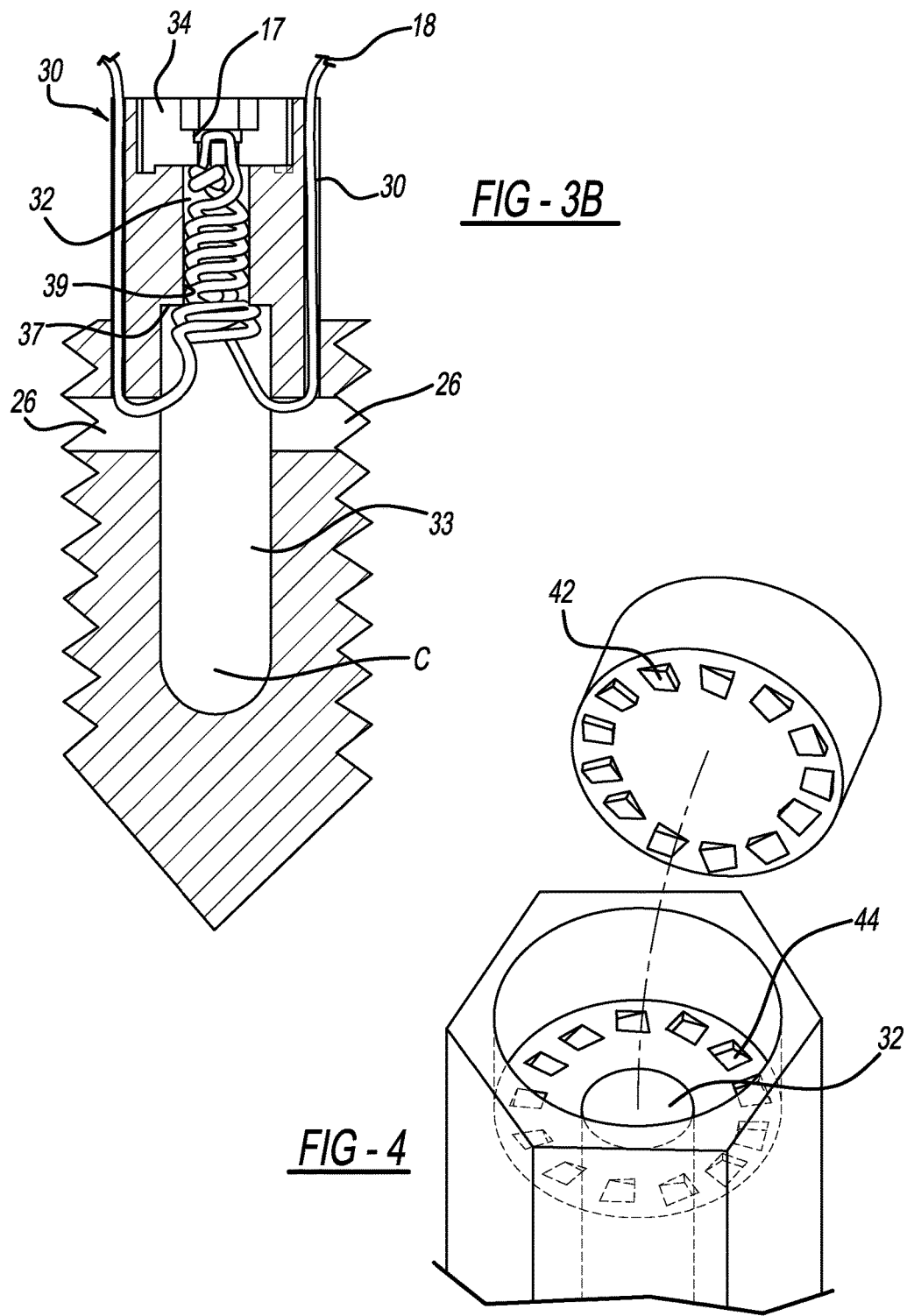

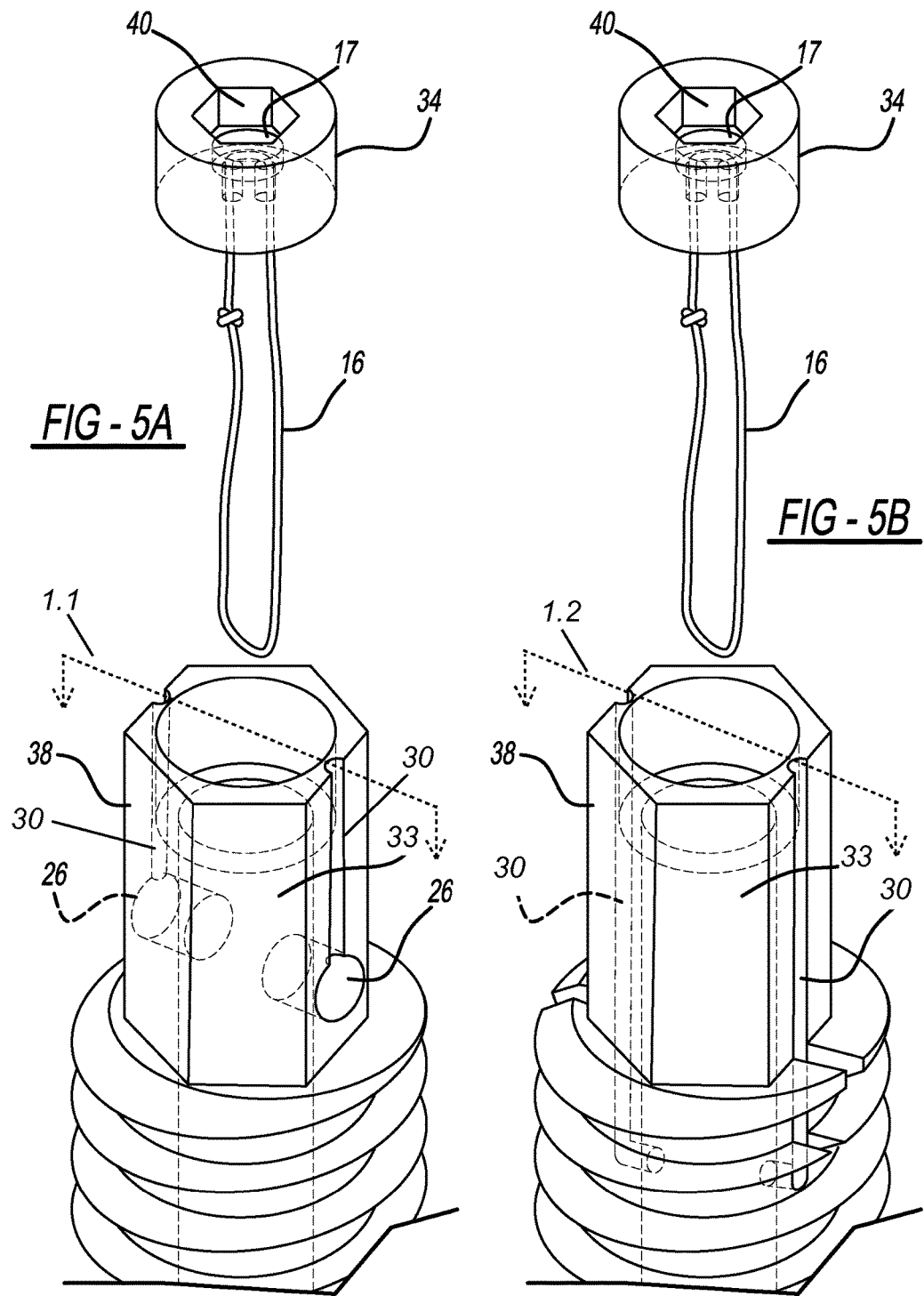

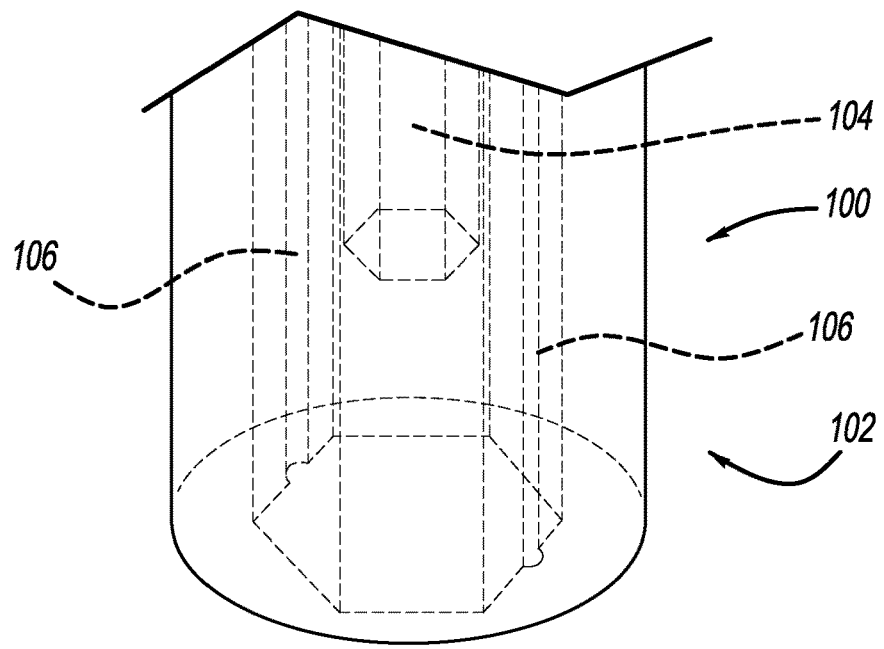
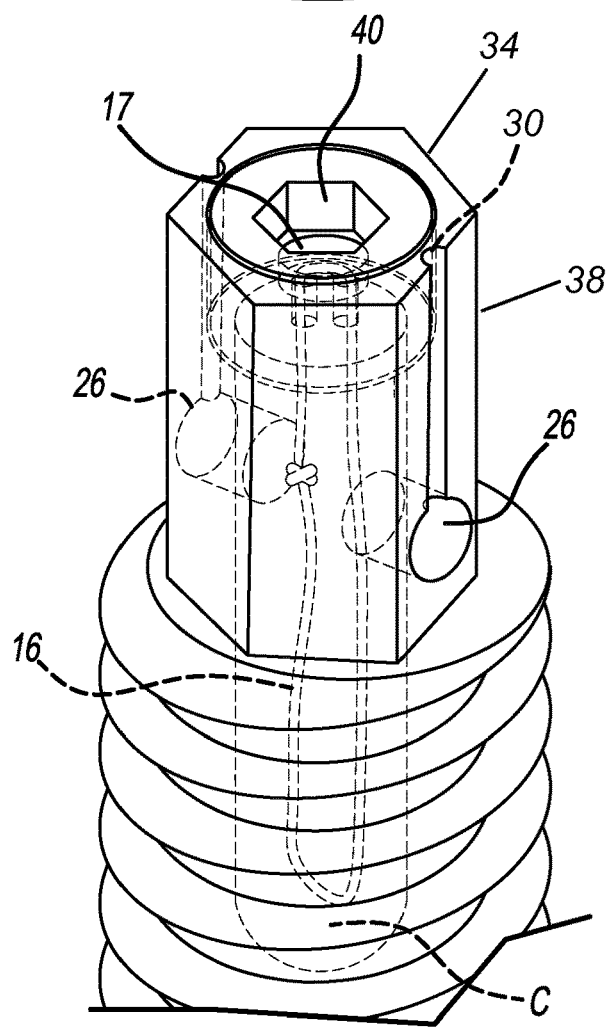
FIG - 6

KNOTLESS TWIST SUTURE ANCHOR

FIELD

The present disclosure relates to methods and apparatuses for securing a suture. In particular, the present disclosure relates to a knotless twist for securing of a suture using a suture anchor.

BACKGROUND

This section provides background information related to the present disclosure which is not necessarily prior art.

Surgical or medical procedures are often performed on a body, for example a human body or anatomy, to repair or replace various portions thereof. For example, the soft tissues of the body may need to be reattached to bones due to trauma, overuse, surgical intervention, or disease.

Soft tissue can be reattached to bone using devices such as screws, staples, and various types of suture anchors. Soft tissues are often fixed to various positions on the bone. For example, to replace a natural tendon fixation point or to replace the tendon itself, fixing a graft to a selected bone area may be desired. One means to fix the soft tissue to the selected area is to provide a suture through a selected portion of the soft tissue and fix the other end of the suture to a selected area on the bone. Various structures can be provided to anchor or hold the suture in the selected bone area. To secure the sutures, the free ends of the suture are generally tied together to form a knot.

The use of knots in surgical procedures, however, can be improved upon. First, in minimally invasive procedures, such as arthroscopic or laparoscopic procedures, the surgical site is not readily accessible and limits the surgeon's ability to tie a knot manually and the site must be secured remotely. One remote method of securing the suture is tying each of the suture ends into a knot extracorporeally and then remotely advancing the knot into the surgical site using suitably configured instruments. Securing the suture remotely can be cumbersome and time consuming.

Second, knots may create stress points in a suture on opposite sides of the knot. When a failure load is applied to a knotted suture, the suture may break at the knot, even though the suture is otherwise free from imperfections.

Accordingly, there is a need for improved devices for securing a suture without a knot. There is a need for surgical methods to facilitate easy and efficient securing of the suture.

SUMMARY

This section provides a general summary of the disclosure, and is not a comprehensive disclosure of its full scope or all of its features.

A suture anchor includes a first body portion having a bone-engaging feature to fixedly engage a bony tissue and a second body portion including a flexible member loop for receipt of a suture where engaging the second body portion rotates the flexible member loop with respect to the first body portion. Rotation of the second body portion causes the flexible member loop to frictionally engage a suture passing through the flexible member loop to form a twist to frictionally secure the suture.

In other features, a suture anchor includes a first body portion having a bone-engaging feature to fixedly engage a bony tissue and a second body portion comprising a fixation point that attaches a flexible member loop for receipt of a suture to the second body portion, where engaging the second body portion applies a rotational torque to the flexible member loop causing the flexible member loop to rotate with respect to the first body portion. The rotational torque causes the rotating flexible member loop to frictionally engage a suture passing through the flexible member loop to form a twist that frictionally secures the suture and draws the flexible member loop toward the second body portion.

In still other features, a threaded suture anchor body having a bone-engaging surface feature to fixedly engage a bony tissue where the suture anchor body has a proximal end and a distal end and a flexible member loop fixedly attached to a rotatable base where the rotatable base and the flexible member loop are located on an interior region of the threaded suture anchor body and are distal to the suture anchor body proximal end. Rotation of the rotatable base causes the flexible member loop to frictionally engage a suture passing through the flexible member loop to form a twist to frictionally secure the suture.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 1 depicts a cross-sectional view of a suture anchor having a rotatable flexible member loop taken along the longitudinal axis of the suture anchor as depicted in FIG. 5A at 1.1 according to various embodiments;

FIG. 2 depicts a cross-sectional view of an alternative suture anchor having a rotatable flexible member loop taken along the longitudinal axis of the suture anchor according to various embodiments;

FIG. 3B depicts a cross-sectional view of another alternative suture anchor having a rotatable flexible member loop taken along the longitudinal axis of the suture anchor as depicted in FIG. 5B at 1.2 according to various embodiments;

FIG. 4 depicts a ratcheting portion of a suture anchor having ratcheting elements to produce one-way rotation of a flexible member loop according to various embodiments;

FIG. 5A depicts a rotatable flexible member loop having a female hex end and a corresponding suture anchor according to various embodiments;

FIG. 5B depicts an alternative rotatable flexible member loop having a female hex end and a corresponding suture anchor according to various embodiments;

FIG. 6 depicts an assembled suture fixation device of FIG. 5;

Corresponding reference numerals indicate corresponding parts throughout the several views of the drawings.

DETAILED DESCRIPTION

Figure 3A:
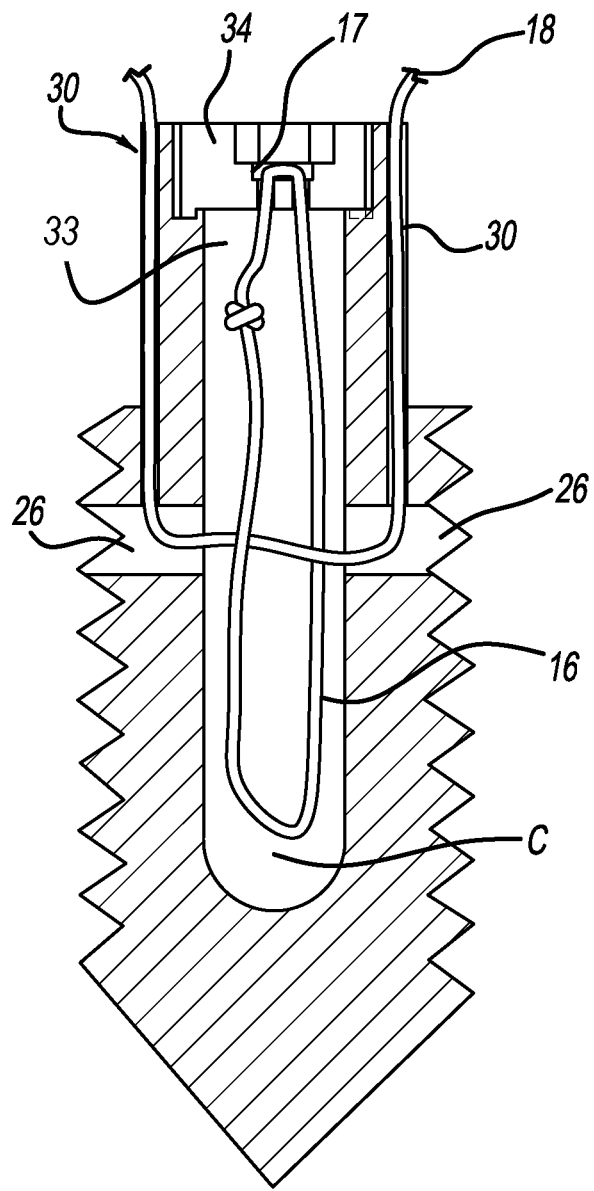
FIG. 3A depicts a cross-sectional view of an alternative suture anchor having a rotatable flexible member loop taken along the longitudinal axis of the suture anchor as depicted in FIG. 5B at 1.2 according to various embodiments.

Example embodiments will now be described more fully with reference to the accompanying drawings.

Referring to FIGS. 1 through 8, a suture fixation apparatus 10 is provided. A first body portion 12 for engaging bone is located at the distal end of the suture fixation apparatus 10. A second body portion 14 is located proximally to the first body portion 12. The second body portion 14 comprises a flexible member loop 16 and fixation point or eyelet 17. The flexible member loop 16 comprises a flexible member, such as a loop formed of a suture, stainless steel, titanium, Nitinol, or other suitable material, comprising a first end 16a and a second end 16b knotted to form the loop 16. The flexible member loop 16 is attached to the second body portion 14 at the fixation point 17. In some implementations, the fixation point 17 defines at least one bore in a side of the second body portion 14. For example, the fixation point 17 may be a recessed portion in the second body portion 14. The recessed portion includes an entrance opening or bore 17a and an exit opening or bore 17b.

As illustrated in FIG. 1, the entrance opening 17a may define a first bore through the second body portion 14 and the exit opening 17b may define a second bored through the second body portion 14. The first end 16a is fed through the entrance opening 17a of the fixation point 17 and passes through the exit opening 17b of the fixation point 17. The first end 16a is brought up and knotted to the second end 16b at or near the first opening of the fixation point 17. In this way, the first end 16a and the second end 16b define the flexible member loop 16. It is understood that while only knotting the flexible member loop 16 to the second body portion 14 is described, the flexible member loop 16 may be secured to the second body portion 14 in any suitable manner. For example, the flexible member loop 16 may be molded into the second body portion 14 during manufacturing. In another example, the fixation point 17 may comprise holes on opposing sides of the second body portion 14. The flexible member loop 16 may be defined by securing the first end 16a to a first opposing side and securing the second end 16b to a second opposing side.

The second body portion 14 is rotatable along a longitudinal axis of the suture fixation apparatus 10 with respect to the first body portion 12. As described in detail below, a suture 18 passes through the flexible member loop 16. Rotating the second body portion 14 causes the flexible member loop 16 to fold on and frictionally engage the suture 18 to form a twist T as illustrated in FIG. 8. The twist T advantageously prevents applying compressive forces from the fixation apparatus 10 onto the suture 18.

In various embodiments, the first body portion 12 can be a suture anchor 20 to engage bone. The suture anchor 20 includes a tip 22, an anchor body shaft 24, and at least one suture-receiving opening or transverse bore 26. The tip 22 is located at the distal end of the first body portion 12. The tip 22 can be formed to substantially ease entry of the anchor 20 into a bony region or can be formed to allow the anchor 20 to be substantially self-drilling or self-tapping. Therefore, the tip 22 can be round or bullet nose, square, substantially sharp, or any other appropriate design to allow for entry of the suture anchor 20 into a selected bony portion.

The anchor body shaft 24 is located proximal to the tip 22. The anchor body shaft 24 can include an attachment feature to engage bone and fixedly hold the first body portion 12 in bone. As shown, the attachment feature includes threads 28. It is understood that other attachment features can be used such as one or several of a spike, pin, ridge, tooth, or another bone-engaging element to fixedly hold the anchor body shaft 24. Various combinations of attachment features can also be used.

The threads 28 can be designed in any appropriate fashion. Non-limiting examples of threads 28 include helical threads, threads with parallel angled surfaces, or annular ridges. The threads 28 generally begin at the distal end of the anchor body shaft 24 and end at the proximal end of the anchor body shaft 24. The threads 28 can be provided in a continuous or discontinuous pitch. The threads 28 can also be limited to only a region of the anchor body shaft 24. In some embodiments, the thread pattern can begin on the tip 22 and continue along the anchor body shaft 24.

Figure 8A:
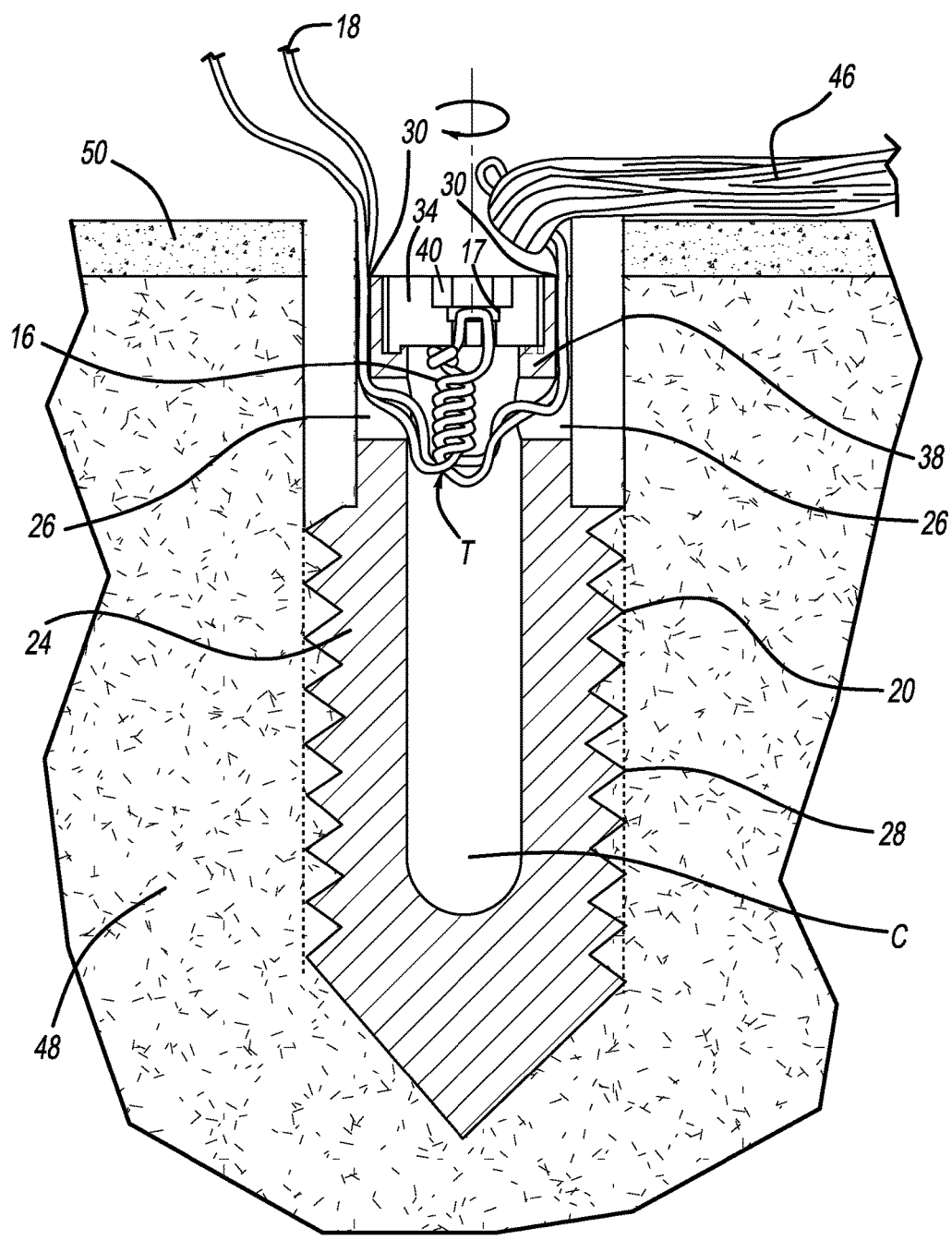
FIG. 8A depicts an alternative environmental view of a suture fixation device according to various embodiments.
Figure 8B:
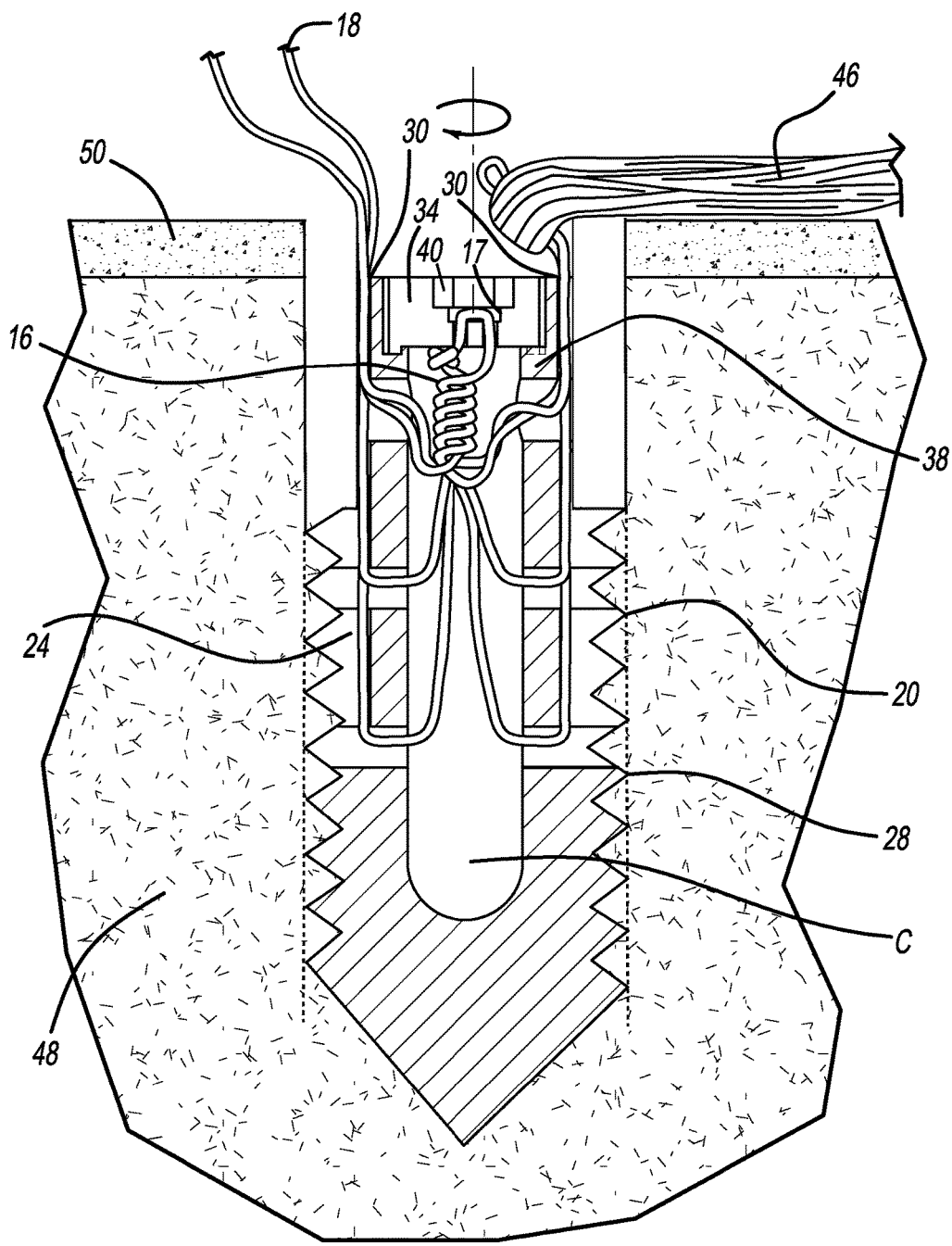
FIG. 8B depicts an alternative environmental view of another suture fixation device according to various embodiments.

The suture-receiving openings or a transverse bore 26 is located at the proximal end of the anchor body shaft 24. Alternatively, the receiving openings 26 may be located nearer the distal end of the anchor body shaft 24 and in the threaded area as illustrated in FIGS. 3A-3B and further described below. In some implementations, the suture fixation apparatus 10 may include multiple receiving openings 26 as illustrated in FIGS. 8A-B. The suture-receiving openings 26 are defined by the first body portion 12 and are adapted for passage of a single suture 18 strand or multiple suture 18 strands. The suture-receiving openings 26 are in communication with the flexible member loop 16. The suture-receiving openings 26 and the flexible member loop 16 can form a continuous pathway along the transverse axis of the suture anchor 20 through which the suture 18 can pass. The suture-receiving openings 26 are transverse to the longitudinal axis of the anchor body shaft 24 and in communication with a bore 33 within the anchor body shaft 24. The bore 33 may extend from a recess 32 that rotatably receives the second body portion 14.

Suture 18 passes through the first suture-receiving opening 26, through the flexible member loop 16, and through the opposing suture-receiving opening 26. The suture-receiving openings 26 can be aligned with the flexible member loop 16 in substantially the same horizontal plane as depicted in FIG. 1. As described later herein, the suture-receiving openings 26 can also be formed as part of the drive end of the suture anchor 20. In various embodiments, it is desirable to have the suture-receiving openings 26 adjacent to opposed vertical channels 30 in the first anchor body 12. The channels 30 can be used to guide the suture 18 along the proximal end of the suture anchor 20. Further, the channels 30 may allow a tool to be used to implant the fixation apparatus 10 while the suture 18 is pre-loaded into the fixation apparatus 10.

The first body portion 12 includes the opening or cylindrical recess 32 for rotatably receiving the second body portion 14 and the flexible member loop 16. The opening or recess 32 can originate at or near the proximal end of the anchor body shaft 24 and extend into the bore 33 that terminates adjacent to the distal tip of the anchor body shaft 24. The opening or recess 32 is sized to allow the corresponding element of the second body portion 14 to rotate about the longitudinal axis of the first body portion 12 to form the twist T in the flexible member loop 16 when the suture 18 passes through the flexible member loop 16. The opening or bore 33 provides sufficient clearance space C for the flexible member loop 16 to twist and frictionally secure the suture 18. The bore 33 (as described above) extends from the proximal end of the first body portion 12 and terminates adjacent to the distal tip 22. The bore 33 is sized to accommodate a predetermined length of the flexible member loop 16. As illustrated in FIGS. 3A-3B, the receiving openings 26 can alternatively be formed more distally in the first body portion 12 adjacent to the distal tip 22. The channels 30 can be used to guide the suture 18 along the anchor body 12 to the receiving openings 26 and can extend through the threaded portion, as shown in FIG. 5B. As illustrated in FIGS. 1, 2, and 3A-3B, the bore 33 extends past the suture-receiving openings 26, allowing the flexible member loop 16 to extend distally past the openings 26.

The bore 33 may extend to a narrowed portion or bore at 39 as illustrated in FIG. 3B. The narrow portion 39 may be arranged at or near the proximal end of the bore 33 and include a shoulder 37. The narrow portion 39 may be cylindrical or polygonal and include faceted sides. The narrow portion 39 is sized to facilitate pinching of the twist T. For example, rotating the second body portion 14 causes the flexible member loop 16 to fold on and frictionally engage the suture 18 to form a twist T. As the second body portion 14 is rotated, a rotational torque is applied to the flexible member loop 16 about the suture 18 drawing the flexible member loop 16 axially toward the second body portion 14. As the flexible member loop 16 is drawn toward the second body portion 14, the twist T may expand to fill the narrowed space provided by the narrow portion 39, thereby pinching or wedging the flexible member loop 16 and the suture 18 within the narrow portion 39. Further, a portion of the flexible member loop 16 may be pinched or wedged against the shoulder 37.

The flexible member loop 16 is adapted to allow the suture 18 to pass therethrough. The flexible member loop 16 is in communication with the suture-receiving openings 26 in the first body portion 12. The flexible member loop 16 can be of any suitable fixed length and can allow for the passage of a single suture, folded or looped suture, or multiple sutures. The suture-receiving openings 26 can also be appropriately shaped or sized to allow for passage of a single suture, folded or looped suture, or multiple sutures.

The second body portion 14 also includes a rotation base 34 to facilitate rotation of the second body portion 14 and the flexible member loop 16. The rotation base 34 fits in (or on) the recess 32 on an annular shoulder 43 of the first body portion 12 and allows for 360° of movement of the second body portion 14 with respect to the first body portion 12. As stated above herein, aligning the flexible member loop 16 with respect to the suture-receiving openings 26 can form a continuous transverse pathway through which the suture 18 can freely slide. Rotating the flexible member loop 16 with respect to the suture-receiving openings 26 on the first body 12 can cause the flexible member loop 16 and the suture-receiving openings 26 to misalign and thereby enhance the securing of the suture 18 by the twist T.

The second body portion 14 can be contained partially in the first body opening or recess 32 or contained fully in the opening or recess 32. The second body portion 14 can also be oriented such that it lies substantially flush with the first body portion 12. Examples of substantially flush include fully co-planar or where the second body portion 14 terminates along the same plane as the terminal plane of the first body portion 12. Substantially flush also includes minor planar variance, such as where the second body portion 14 terminates with a slight (less than 10% of suture fixation apparatus total length) positive arcuate or other varying non-planar surface (ridges or a slot mated to a screw driver, for example) with respect to the first body portion 12.

The suture fixation apparatus can include a drive end 38 to receive a tool or driver. The drive end 38 is located at a proximal end of the first portion body 12, as shown, for example, in FIG. 2. The drive end 38 can be defined by a part of the first body portion 12 which extends equal to or proximal to the second body portion 14, as shown in FIG. 5A. The drive end 38 can include a substantially hexagonal perimeter to be received within a drive tool 100, as shown in FIG. 6. As a further example, various features can be formed substantially on the end of the drive end 38 to be operated by a screw driver having a complementary blade. The driver end 38 can be formed to facilitate advancement of the suture anchor 20 by screwing, impacting, pushing, or combinations thereof, for example, or other suitable techniques.

As best depicted in FIGS. 5A, 5B, and 6, the second body portion 14 can be received by the drive end 38. A tool-engaging region 40 on the second body 14 can be formed to mate with a hex driver as shown in FIG. 6, with a screw driver, or any other suitable drive tool 100. The tool-engaging region 40 may include indicia (not shown) such as a line, mark, or groove that indicates a position of the tool-engaging region 40 corresponding to a position of the flexible member loop 16. For example, the indicia can indicate whether or not the flexible member loop 16 is aligned with the suture-receiving openings 26 as described above. As illustrated in FIG. 6, the tool 100 may include a first driver portion 102 and a second driver portion 104. The first driver portion 102 is formed to receive the drive end 38. Similarly, the second driver portion 104 is formed to mate with the tool-engaging region 40. The first driver portion 102 and the second driver portion 104 may cooperatively operate to drive the fixation apparatus 10. For example, the tool 100 may drive the drive end 38 and the tool-engaging region 40 simultaneously. Alternatively, the first driver portion 102 may operate independently from the second driver portion 104. In other words, the first driver end 102 may drive the anchor body shaft 24 without acting upon the tool-engaging region 40. Similarly, the second driver end 104 may drive the tool-engaging region 40 without acting upon the drive end 38. In this manner, the tool 100 may drive the anchor body shaft 24 without engaging the flexible member loop 16.

The tool 100 may also include suture channels 106. The suture channels 106 allow a suture to be preloaded into the fixation apparatus 10. For example, the suture 18 may be preloaded in the fixation apparatus 10. The suture 18 is guided by the channels 30, as shown in FIGS. 1 and 3. Alternatively, as shown in FIG. 2, the suture 18 is passed through the suture-receiving openings 26. The suture channels 106 provide a clearance for the suture 18 in order to prevent the tool 100 from disturbing a position of the suture 18. In this manner, the tool 100 can drive the drive end 38 without damaging or displacing the suture 18. The tool-engaging region 40 performs multiple functions including being adapted to facilitate insertion of the suture anchor 20 and/or adapted to facilitate rotation of the flexible member loop 16 to form the suture twist T around the suture 18.

In an exemplary use of the tool-engaging region 40 in accordance with FIGS. 5A, 5B, and 6, a hex female driver is used to fit over the drive end 38 of the first body member 12 to advance the suture anchor 20 into a bony tissue. A male hex driver is inserted into the tool-engaging region 40 to rotate the second body portion 14 and cause the flexible member loop 16 to axially twist on the suture 18 to form the twist T. As the second body portion 14 is rotated, a rotational torque is applied to the flexible member loop 16 about the suture 18 drawing the flexible member loop 16 toward the second body portion 14, as illustrated in FIG. 3B. In this way, the flexible member loop 16 applies a vertical or axial force and a horizontal force on the suture 18, thereby securing the suture 18 to the suture anchor 20.

It is appreciated that the hex female driver and the male hex driver can be formed as a single tool. For example, this exemplary driver is the mirror image of the drive end 38 and tool-engaging region 40 as depicted in FIGS. 5A, 5B, and 6. The tools, the drive ends 38, and tool-engaging regions 40, as described above can be modified to facilitate use of any suture fixation device 10 according to the present teachings.

The suture fixation device 10 can be made of a resorbable biocompatible material. The suture fixation device 10 can be formed of a polymer or a co-polymer, such as a co-polymer of polylactic acid and polyglycolic acid LACTOSORB as sold by Biomet, Inc. of Warsaw, Ind. Suitable polymers also include any other organic polymers (or co-polymers), such as polyethylene, polyetheretherketone (PEEK), and polyetherketoneketone (PEKK), as non-limiting examples. The suture fixation device 10 can be formed of a metal, such as titanium, stainless steel, or alloys of cobalt, chromium, etc.; a ceramic material; or any calcium-containing materials including, but not limited to monobasic, dibasic, and tribasic calcium phosphates and hydroxyapatite. The suture fixation device 10 can also be made of a composite of any of the above materials. Regardless of the selected materials, the suture fixation device 10 is formed such that it will have a selected pull-out strength to substantially hold the suture fixation device 10 in position after the device has been implanted into the bone.

Referring to FIGS. 1-4, the suture fixation device 10 can include a ratcheting mechanism at the annular shoulder 43 to provide one-directional movement of the second body portion 14 with respect to the first body portion 12. As illustrated in FIG. 4, the ratcheting mechanism can include at least one ridge 42, located on one of the first body portion 12 or the second body portion 14 and a corresponding pawl 44 located on the other body portion. As shown, the ratcheting components are placed on the rotating base 34 of the second body 14 and the proximal end of the first body 12 which abuts the rotating base 34. The one-directional movement allows turns to be placed on the twist T while preventing unintentional reduction in frictional force between the winds of the flexible member loop 16. In other words, the twist T will not unwind.

Figure 7:
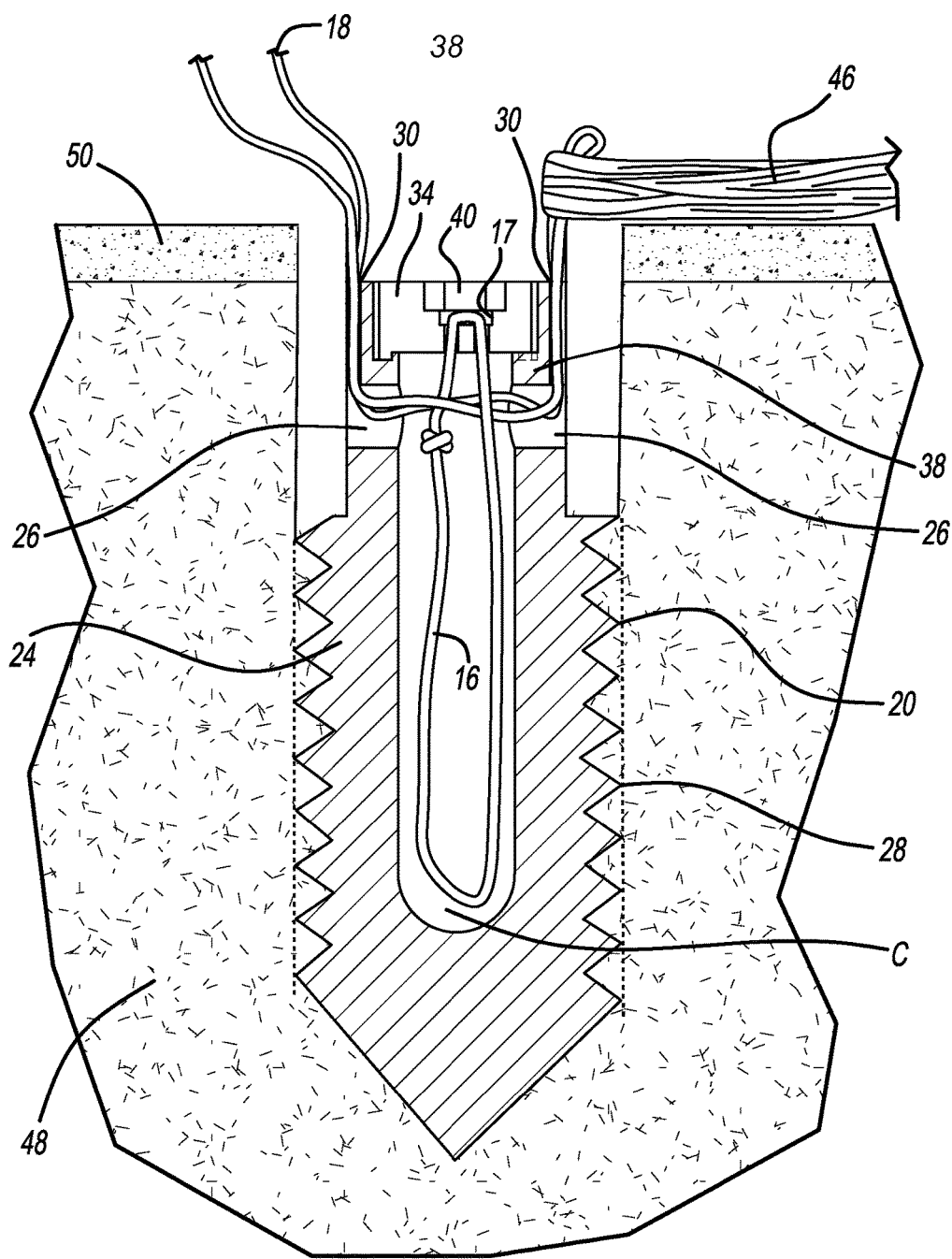
FIG. 7 depicts an environmental view of a suture fixation device according to various embodiments.

An exemplary use of the suture fixation device 10 is depicted in FIGS. 7, 8A, and 8B. The suture 18 is disposed in the flexible member loop 16 and through the suture-receiving openings 26. In an embodiment where multiple suture-receiving openings 26 are employed, a separate suture 18 or multiple suture strands are passed through the suture-receiving openings 26 and the flexible member loop 16. As illustrated in FIG. 8A, multiple suture strands may pass through a single pair of suture-receiving openings 26. Alternatively, as illustrated in FIG. 8B, multiple sutures may pass through a plurality of pairs of suture-receiving openings 26. For example, a first suture may pass through a first pair of suture-receiving openings 26 positioned at or near the proximal end of the first body portion 12, while second and third sutures pass through a second pair and third pair of suture-receiving openings 26, respectively, adjacent to the distal tip 20. It is understood that while only three pairs of suture-receiving openings 26 are described, any suitable number of pairs of suture-receiving openings 26 are contemplated by the principles of the present disclosure.

The suture fixation device 10 is placed into bone such that the first body portion 12 is fixedly attached to bone and does not rotate. The suture fixation device 10 can be placed into bone via the drive end 38 and a corresponding driver, such as the first driver portion 102. Suitable placement techniques depend on the style of the suture fixation device or the bone-engaging features of the suture fixation device 10. For example, threading the suture fixation device 10 into bone or impacting the suture fixation device 10 into a pre-formed opening in bone.

In various embodiments, the suture 18 is preloaded and passes through the flexible member loop 16 prior to placement of the suture fixation device 10 such that the suture 18 and the suture fixation device 10 are implanted in a single action or step. In other embodiments, the suture 18 can be loaded in the flexible member loop 16 after the suture fixation device 10 has been placed in the bone. As described above, the flexible member loop 16 is fixedly attached to the second body portion 14 at the fixation point 17. It is understood that the flexible member loop 16 can be pre-loaded or attached to the fixation point 17 prior or alternatively, the flexible member loop 16 can be attached to the fixation point 17 after the suture fixation device 10 has been placed in the bone.

Once the first body portion 12 is fixedly attached and the suture 18 is placed, the second body portion 14 is engaged through the rotation base 34 and/or tool-engaging region 40. Engagement of the rotation base 34 and/or the tool-engaging region 40 can be achieved using the second driver portion 104 or the tool 100. The rotation base 34 is rotated in a single direction to cause the flexible member loop 16 to wind upon the suture 18 to form the twist T. The folds of the twist T provide friction between the strand of the flexible member loop 16 and the strand of the suture 18 and cause the suture 18 to tighten thereby preventing the unintentional removal of the suture 18 from within the suture fixation device 10. Rotating the rotation base 34 causes a rotational torque to be applied to the flexible member loop 16 about the suture 18. The rotational torque causes the flexible member loop 16 to twist and draw the suture 18 into folds of the twist T. Continuing to rotate the rotation base 34 applies an eccentric axial force on the flexible member loop 16. The axial force draws the twisted flexible member loop 16 toward the second body portion 14, thereby minimizing or preventing movement of the suture 18 in both axial and transversal direction.

In various embodiments the suture 18 is secured by rotating the rotation base 34 at least 10 times to cause 10 turns of the flexible member loop 16. The suture 18 can also be secured by as few as 2 twists or as many as 25 twists, or any suitable number of twists as needed. The twisting can be achieved manually as the surgeon's hands rotate the rotation base 34. In embodiments requiring a higher number of twists, a tool having a rotation amplifying gear or mechanism can be used to turn or drive a single manual rotation into multiple twists.

In embodiments having the ratcheting mechanism, the rotation base 34 is rotated in a single direction to cause the flexible member loop 16 to wind on the suture 18 form the twist T. In the example as described above, the ridges 42 of the first body portion and the pawls 44 on the second body portion pass each other thereby tightening the twist T and thereby securing the suture 18.

The suture fixation device 10 can be advantageously used to finely tighten a soft tissue 46. The suture 18 is looped through the tissue and through the flexible member loop 16 and suture openings 26. A folded loop is generally through the tissue and the free ends of the folded loop extend out of the hole in bone. The free ends of the suture 18 are held tightly (by hand or with any suitable surgical device) and the suture fixation device 10 is rotated to tighten the suture 18 and secure the tissue 46 in or adjacent to the opening in bone.

The suture fixation device of the present disclosure is useful to secure a suture or sutures to a defect site. The methods are useful for a variety of soft tissue repairs including, but not limited to, rotator cuff repairs, labral repairs, glenoid repairs, and medial collateral ligament repairs. The suture fixation device detailed above can be used in conjunction with the methods.

For example, a method for repairing a damaged rotator cuff may include preloading the suture fixation apparatus 10 with a flexible member loop 16 and at least one suture 18 onto the tool 100. Alternatively, the at least one suture 18 may be loaded into the suture fixation apparatus 10 after the suture fixation apparatus 10 is fixed to a bony tissue 48. A suture 18 is passed through a rotatable region of a suture fixation apparatus 10. For example, the suture 18 passes through suture-receiving openings 26 provided in the first body portion 12. The suture 18 can be passed through the flexible member loop 16 of the suture fixation device 10. The suture fixation device 10 is then fixed to a bony tissue 48 adjacent to a cortical bone 50 to prevent movement of a region of the fixation device 10. The fixation is achieved by using the bone-engaging attachment features 28 as detailed earlier herein. For example, the first driver portion 102 may drive the drive end 38 thereby driving the first body portion 12 into the bony tissue 48. The rotatable region containing the flexible member loop 16 is rotated to form a twist in the flexible member loop 16 around the suture 18 frictionally secure the suture 18 and tightening the soft tissue. For example, the second driver portion 104 engages the tool-engaging reading 40. The second driver portion 104 is rotated there by rotating the flexible member loop 16. Rotating the flexible member loop 16 forms a twist in the flexible member loop 16, thereby frictionally securing the suture 18 within the winds of the twist T in the flexible member loop 16.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A suture anchor comprising:
   a first body portion having a bone-engaging feature to fixedly engage a bony tissue; and
   a second body portion rotatable relative to the first body portion and having a flexible member loop coupled to the second body portion and configured for receipt of a suture; wherein rotation of the second body portion relative to the first body portion rotates the flexible member loop and is configured to cause the flexible member loop to fold upon and to frictionally engage a suture passing through the flexible member loop to form a twist to frictionally secure the suture passing through the flexible member loop, wherein the second body portion includes a recessed fixation point including a cavity on a bottom surface of a tool engaging region of the second body portion where the flexible member is coupled to the second body portion by extending through holes located on the bottom of the tool engaging region which extend into the cavity of the recessed fixation point such that the flexible member is exposed within the tool engaging region of the second body member while being recessed below the tool-engaging region.

2. The suture anchor according to claim 1, wherein the second body portion is located at a proximal end of the suture anchor.

3. The suture anchor according to claim 1, wherein the first body portion defines a recess.

4. The suture anchor according to claim 3, wherein the second body portion is at least partially contained in the recess.

5. The suture anchor according to claim 1, wherein the second body portion includes an entrance bore and an exit bore.

6. The suture anchor according to claim 5, wherein a first end of a second suture passes through the entrance bore and through the exit bore.

7. The suture anchor according to claim 6, wherein the first end is knotted to a second end of the second suture to form the flexible member loop.

8. The suture anchor according to claim 1, wherein the suture anchor comprises a drive end to receive a driver and advance the suture anchor by a technique selected from the group consisting of:
   impacting, screwing, pushing, and combinations thereof.

9. The suture anchor according to claim 1, further comprising a ratcheting mechanism to provide one-directional movement of the second body portion with respect to the first body portion.

10. The suture anchor according to claim 9, wherein the ratcheting mechanism comprises at least one ridge located on one of the first body portion and said second body portion and at least one pawl disposed opposite the ridge located on the other of the first body portion and the second body portion.

11. The suture anchor according to claim 1, further comprising a first suture-receiving opening located on an opposed side of the first body portion from a second suture-receiving opening.

12. The suture anchor according to claim 1, wherein the first suture-receiving opening and the second suture-receiving opening are in communication with a longitudinal bore defined by the first body portion, where the longitudinal bore receives the flexible member loop.

13. A method for securing a suture of a suture anchor comprising:
   driving a first body portion of the suture anchor into a bony tissue, the first body portion having a bone-engaging feature to fixedly engage the bony tissue; and
   rotating a second body portion of the suture anchor, the second body portion rotatable relative to the first body portion, where rotating the second body portion applies a rotational torque to a flexible member loop coupled to the second body portion causing the flexible member loop to rotate with respect to the first body portion;
   forming a twist in the flexible member loop about a suture extending through the flexible member loop, in response to the rotational torque, that causes the flexible loop member to fold upon and frictionally engage the suture passing through the flexible member loop to frictionally secure the suture and draw the flexible member loop toward the second body portion, wherein the second body portion includes a recessed fixation point including a cavity on a bottom surface of a tool engaging region of the second body portion where the flexible member is coupled to the second body portion by extending through holes located on the bottom of the tool engaging region which extend into the cavity of the recessed fixation point such that the flexible member is exposed within the tool engaging region of the second body member while being recessed below the tool-engaging region.

14. The method according to claim 13, further comprising passing the suture through a transverse bore aligned with the flexible member loop.

15. The method according to claim 14, further comprising attaching a first end of the suture to a portion of soft tissue.

16. The method according to claim 15, further comprising passing a second end of the suture through the flexible member loop.

17. The method according to claim 16, further comprising applying a tension to the second end of the suture to secure the soft tissue.

18. The method according to claim 17, further comprising frictionally securing the suture by rotating the second body portion forming the twist in the flexible member loop about the suture and securing the second end of the suture to a portion of bone.

19. The method according to claim 13, further comprising rotating the second body portion independent of the first body portion, wherein the flexible member loop rotates in response to the second body portion being rotated and wherein the suture is frictionally secured within the twist of the flexible member loop.

20. A suture anchor comprising:
a suture;
a first body portion extending along a longitudinal axis from a proximal end to a distal end, the first body portion defining a longitudinally extending bore extending from a recess in the proximal end to the distal end and a transverse bore open to the longitudinally extending bore, and at least one suture channel in communication with the transverse bore and extending along an outer surface of the first body portion perpendicularly to the transverse bore, the first body portion having a bone-engaging feature to fixedly engage a bony tissue; and
a second body portion rotatably received in the first body portion and rotatable relative to the first body portion and coupled to a flexible member loop disposed in the longitudinally extending bore, the flexible member configured to receive the suture, wherein the second body portion includes a recessed fixation point including a cavity on a bottom surface of a tool engaging region of the second body portion, the recessed fixation point including a first bore extending from a top surface to a bottom surface of the second body portion and a second bore extending from the top surface to the bottom surface of the second body portion, the first and second bores being open to the cavity of the recessed fixation point, where the flexible member is coupled to the second body portion such that the flexible member goes through the first bore and the second bore and is exposed within the tool engaging region at the top surface of the second body member while being located below the tool-engaging region of the second body portion;
wherein rotation of the second body portion relative to the first body portion rotates the flexible member loop and causes the flexible member loop to fold upon and to frictionally engage the suture passing through the flexible member loop to form a twist that frictionally secures the suture.

21. The suture anchor according to claim 20 wherein the at least one suture channel guides an end of the suture along a side of the suture anchor.

22. The suture anchor according to claim 20 in combination with a drive tool that includes a first drive portion and a second drive portion.

23. The suture anchor and drive tool according to claim 22 wherein the first drive portion drives the first body portion and the second drive portion rotates the second body portion relative to the first body portion.

24. The suture anchor and drive tool according to claim 23 wherein the first drive portion and the second drive portion cooperatively operate.

25. The suture anchor according to claim 23 wherein the first drive portion and the second drive portion independently operate.

26. The suture anchor according to claim 20 further comprising a ratcheting mechanism comprising at least one ridge on the first body portion and at least one corresponding pawl on the second body portion.

27. The suture anchor according to claim 26 wherein the at least one ridge and the at least one corresponding pawl cooperatively operate to prevent a reverse rotation of the second body portion.

28. The suture anchor according to claim 20 wherein rotation of the second body portion relative to the first body portion rotates the flexible member loop and draws the flexible member loop toward the second body portion.

29. The suture anchor according to claim 20 wherein the longitudinally extending bore includes a proximal narrowed portion.

30. The suture anchor according to claim 29 wherein rotation of the second body portion relative to the first body portion rotates the flexible member loop and pinches the flexible member loop within the proximal narrowed portion.

* * * * *